(12) United States Patent
Fuhr

(10) Patent No.: US 8,241,906 B2
(45) Date of Patent: Aug. 14, 2012

(54) MAGNETIC MANIPULATION OF BIOLOGICAL SAMPLES

(75) Inventor: Gunter Fuhr, Berlin (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 823 days.

(21) Appl. No.: 10/591,068

(22) PCT Filed: Feb. 25, 2005

(86) PCT No.: PCT/EP2005/002004
§ 371 (c)(1),
(2), (4) Date: Aug. 30, 2006

(87) PCT Pub. No.: WO2005/083057
PCT Pub. Date: Sep. 9, 2005

(65) Prior Publication Data
US 2008/0038806 A1    Feb. 14, 2008

(30) Foreign Application Priority Data
Mar. 1, 2004  (DE) .......................... 10 2004 009 985

(51) Int. Cl.
*C12N 11/00* (2006.01)
*C12N 13/00* (2006.01)
*C12M 1/00* (2006.01)

(52) U.S. Cl. ..................... 435/395; 435/174; 435/307.1; 435/173.1

(58) Field of Classification Search ............... 435/173.1, 435/174, 30.1, 395
See application file for complete search history.

(56) References Cited

U.S. PATENT DOCUMENTS

| 6,355,491 B1 | 3/2002 | Zhou et al. |
| 6,368,838 B1 | 4/2002 | Singhvi et al. |
| 2002/0106314 A1* | 8/2002 | Pelrine et al. .................. 422/186 |
| 2002/0187504 A1* | 12/2002 | Reich et al. ....................... 435/6 |

FOREIGN PATENT DOCUMENTS

| CN | 1289842 | 4/2001 |
| DE | 279 984 | 6/1990 |
| DE | 196 44 761 | 2/1998 |
| DE | 100 27 608 | 12/2001 |
| EP | 1 270 068 | 1/2003 |
| EP | 1 291 413 | 3/2003 |
| WO | WO 03/043931 | 5/2003 |
| WO | WO 2004/034012 | 4/2004 |

OTHER PUBLICATIONS

International Search Report for PCT/EP2005/002004 mailed Aug. 22, 2005.

* cited by examiner

*Primary Examiner* — Taeyoon Kim
(74) *Attorney, Agent, or Firm* — Pearl Cohen Zedek Latzer, LLP

(57) ABSTRACT

The invention relates to a cell carrier (10) for receiving a biological sample. The carrier comprises a magnetic element (20) and a floor element (30) that forms a stable support (31) that can be displaced on a solid base surface in at least one direction. The invention also relates to a manipulation device for biological samples and to a method for manipulating biological samples.

6 Claims, 7 Drawing Sheets

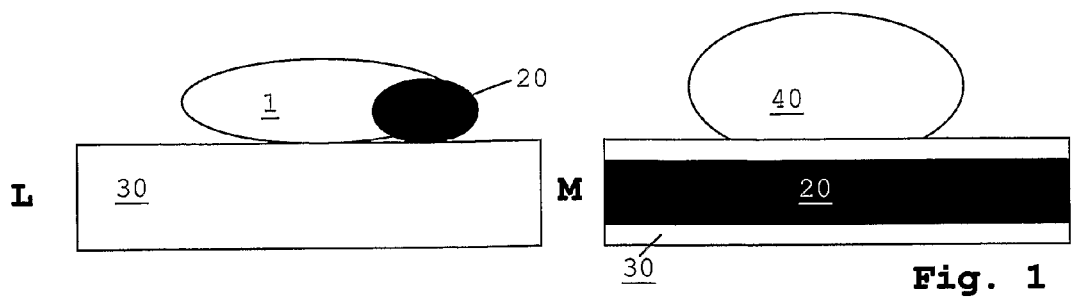
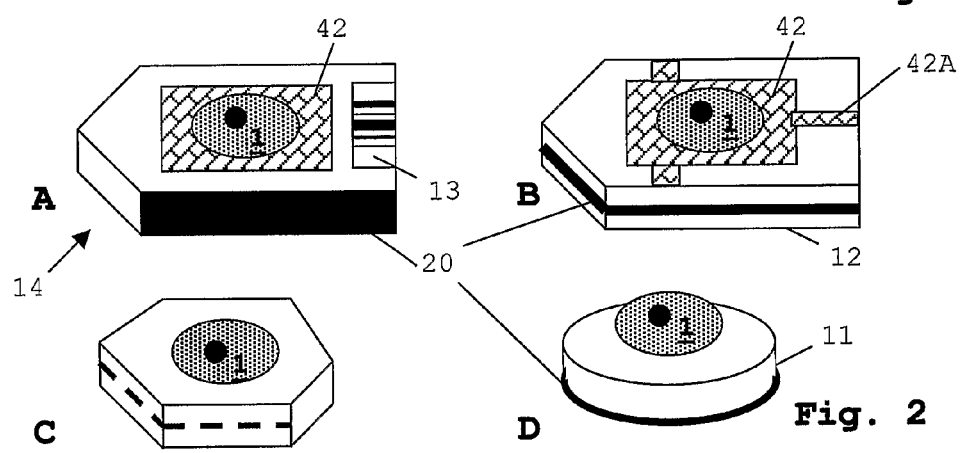
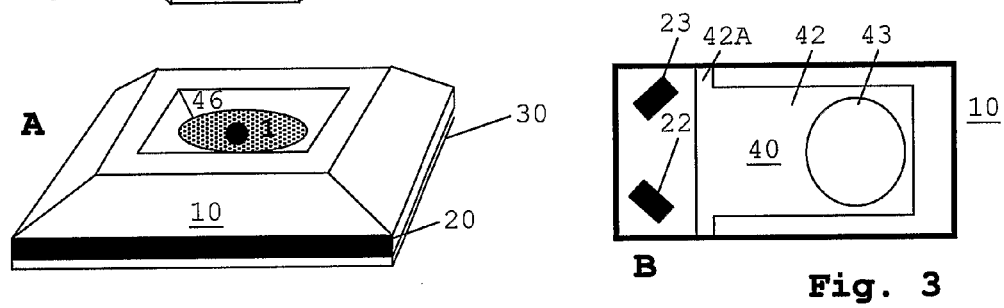
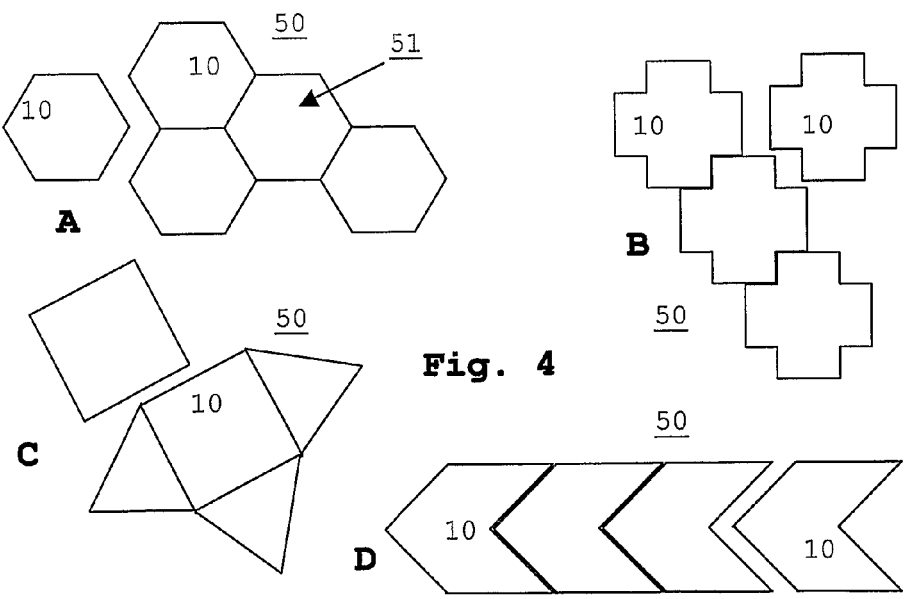

MAGNETIC MANIPULATION OF BIOLOGICAL SAMPLES

PRIOR APPLICATION DATA

The present application is a national phase application of International Application PCT/EP2005/002004, entitled "MAGNETIC MANIPULATION OF BIOLOGICAL SAMPLES" filed on Feb. 25, 2005, which in turn claims priority from German Patent Application DE 102004009985.5, filed on Mar. 1, 2004, all of which are incorporated by reference in their entirety.

FIELD OF THE INVENTION

The invention relates to cell carriers having the features of the preamble of claim 1, to culture carriers which comprise a plurality of such cell carriers, to manipulation devices for using such cell carriers in order to manipulate biological samples, and to methods for manipulating biological samples, such as cells and/or cell components for example.

BACKGROUND OF THE INVENTION

Important aims in biotechnology and medicine consist in generating and processing cell groups and cell assemblies comprising individual biological cells in a manner that is as automated as possible. For example, cells having the desired properties have to be grouped together, treated, multiplied or generally subjected to spatial and/or temporal manipulation. One essential prerequisite for cell cultivation is contact of the biological cells with a solid surface (adherent cells). Many cell types that are relevant for cell therapies or in biotechnology (e.g. fibroblasts, macrophages, lymphocytes, stem cells) cannot survive or at least cannot divide without this contact. Molecularly masked or microstructured and nanostructured surfaces are thus becoming increasingly important.

In practice, miniaturized systems in the form of so-called "bio-labs on a chip" have proven to be advantageous, in particular due to the desired sterility and low costs. These are often produced as a fluidic microchannel system with for example optical or electrical functional components for separating, treating, grouping and characterizing biological cells. However, one disadvantage of the conventional microchannel systems is that, in these, the cells can be moved only in the suspended state in which they are not bound to solid surfaces, for example by means of passive flows, by means of electric fields (electroosmosis, dielectrophoresis, electrophoresis) or by means of optical forces. The abovementioned contacts with solid surfaces are thereby ruled out. However, if the cells do adhere to surfaces, detachment is usually difficult and is possible only via a biochemical route (trypsinization) or with a high level of mechanical stress and cell losses.

Therefore, cell treatments with surface or cell contacts or cultivations of cells can be carried out only to a limited extent using the conventional microchannel systems. There are currently no practical aids for manipulating adherent cells. Adherent cells cannot move individually either relative to the channel system or relative to one another. However, since the adhesion of the cells is of primary importance, there is a great need here for a technique which can be used in the research laboratory and in industry, particularly when carrying out medical cell therapies.

It is known to couple biological cells in suspension to magnetic particles (so-called nanobeads or microbeads), in order then to carry out a cell movement using an external magnetic field. The use of magnetic beads which have a spherical geometry has to date been restricted to the non-specific manipulation of cell groups (for example when collecting suspended cells). The handling of bead-coupled cells individually or in a defined position has to date not been possible. Bead/cell complexes exhibit strong interactions, so that undesirable aggregations (particle/particle interactions via the magnetic field or the surfaces) can rapidly occur. Furthermore, the problem of removing bead/cell complexes individually from a suspension has to date not been solved.

SUMMARY

The objective of the invention is to provide improved techniques for manipulating biological samples, such as cells, cell groups, cell components or biologically active substances for example, by means of which the disadvantages and limitations of the conventional fluidic microsystems can be overcome. In particular, a possibility is to be provided for moving or positioning biological samples individually or in groups in the adherent state in which they are bound to a solid phase and/or for bringing them into contact with one another in a defined manner, wherein the highest possible flexibility in terms of the usability of, for example, biochemical, genetic engineering, medical or biological process techniques is to be achieved. With the invention, a possibility is also to be provided for reliably manipulating adherent cells individually and under sterile conditions.

This objective is solved by a cell carrier which has the features of claim 1, a culture carrier which has the features of claim 30 and which is composed of a plurality of such cell carriers, a manipulation device for biological samples which has the features of claim 36, and a method for manipulating biological samples which has the features of claim 46. Advantageous embodiments and applications of the invention emerge from the dependent claims.

In terms of the device, the present invention is based according to a first aspect on the general technical teaching of providing a cell carrier for receiving a biological sample, which contains at least one magnetic element that makes it possible to move or position the cell carrier by means of a magnetic force, wherein a bottom element is provided, by means of which the cell carrier can be placed and shifted on a solid support surface in a mechanically stable manner. By providing the bottom element, which forms a support on an underside of the cell carrier, positional stability of the cell carrier is advantageously achieved both in the rest state and in the state in which it is moved in particular by the magnetic force. The stability of the cell carrier means that the latter can be arranged without tilting on the solid surface, which hereinafter will be referred to as the base surface or floor surface. No changes in orientation of the cell carrier relative to the base surface are possible, such as for example a tilting movement, falling over or complete inversion by 180°. Advantageously, cell carriers according to the invention can be displaced on the base surface in a predetermined manner solely by the exertion of the magnetic force. The magnetic force is generated by a magnetic interaction of the magnetic element, which contains a magnetic and/or a magnetizable material, with an external magnetic field or an external magnetizable material.

Advantageously, the disadvantages of conventional magnetic microbeads are overcome by the ability of the cell carrier to rest or be moved in a stable manner on a solid base surface. In particular, it is possible to rule out non-reproducible aggregations of microbeads. The conventional bead-based manipulation of cells furthermore does not offer the possibility of providing planar and complex structured surfaces for cell growth in a predefinable size and of a predefinable nature.

Preferably, the cell carrier with the magnetic element comprises on its underside the bottom element, which forms the stable support that can be displaced on a solid base surface in at least one direction, and on its upper side a receiving element which has a surface for receiving the biological sample. According to one feature, which is preferred because of its advantages but is not absolutely necessary, the receiving element is modified so as to promote adhesion at least in a predetermined partial region of its surface, that is to say it has a coating and/or structuring to which the biological cells preferably adhere. For practical use, it is particularly preferred if the adhesion-promoting coating and/or structuring is provided in one partial region of the surface and an adhesion-reducing coating is provided in another partial region of the surface, wherein the partial regions may be contiguous with one another or separate from one another.

Cell carriers according to the invention are preferably plates which contain or carry magnetic materials or magnetizable parts, wherein the cell carriers are designed to receive forces and form a culture platform and surface for cells. The cell carriers can be moved by miniaturized x,y,z manipulators which are guided outside a culture vessel or microsystem. Depending on the size of cells, these systems can be miniaturized down to the micrometer range and are in any case smaller than the typical dimensions of the walls of the culture vessel. The cell carriers may be coated with materials which ensure both the ability to slide on the walls and also the biocompatibility with the cells. A wide range of material combinations, material anisotropies and material gradients is possible.

The bottom element of the cell carrier according to the invention can be formed in a manner depending on the specific application and in particular on the configuration of the base surface on which the cell carrier is to be used. In general, the surface shape of the bottom element may have any shape complementary to the base surface, wherein the bottom element has in at least one direction a straight shape that is free of any curvature, due to the desired shiftability.

According to one preferred embodiment of the invention, the bottom element has a flat and unstructured surface structure. Advantageously, a flat, smooth support is formed, which can be freely displaced parallel to the base surface in all directions, in particular on a flat base surface. Alternatively, the bottom element may have a surface shape which forms a flat, structured support. By way of example, three or more support points may be provided which lie in a common plane and in a corresponding-manner also form a flat support of the cell carrier according to the invention. In this case, advantages are obtained in terms of reduced friction of the cell carrier with respect to the base surface. According to another alternative, the bottom element may have a certain support profile which is complementary to the base surface on which the cell carrier is to be used. Advantageously, by defining the support profile, a movement direction of the cell carrier on the base surface can be fixedly predefined in the manner of a movement on rails. In general, the support profile of the surface shape of the bottom element may be completely concave or convex, or else may be concave and convex in partial regions. If the support profile has a circular cross section, so that the bottom element forms a section of a straight circular cylinder, advantages may be obtained with regard to use of the cell carrier on base surfaces that are curved in a cylindrical manner.

Since the bottom element of the cell carrier according to the invention primarily has a mechanically stabilizing function, there are no restrictions in terms of the material of the bottom element. However, advantages for disruption-free movement of the cell carrier by means of minimal magnetic forces may be obtained if the bottom element is made from a material with reduced adhesion with respect to other solid materials, or at least has a coating made from such a material. Preferably, use is made of polytetrafluoroethylene (PTFE) or another plastic material with comparably low adhesion. PTFE has additional advantages since it is inert for the uses which are in practice of interest when manipulating biological cells or cell cultures.

According to one preferred embodiment of the cell carrier according to the invention, the latter is equipped with the abovementioned receiving element which has a surface for receiving the biological sample, wherein this surface points in a different direction to the bottom element. Usually, the receiving element is formed on a side of the cell carrier which lies opposite the bottom element. The fact of providing the receiving element has the advantage that a defined and delimited geometric region is created for the biological sample, which region can be configured in a specific manner depending on the properties of the sample and the specific use of the cell carrier. The cell carrier can be moved with the sample, whereas the latter is essentially unable to move relative to the cell carrier (apart from natural orientation movements, e.g. of biological cells). Another advantage of the receiving element is the fact that it provides protection for the magnetic element against external influences. The receiving element forms a cover which separates the magnetic element from a surrounding fluid or from a sample arranged on the cell carrier.

The receiving element provided on the upper side of the cell carrier may advantageously be formed with a predetermined surface shape in order to expand the functionality of the cell carrier or to adapt the surface of the receiving element for certain samples. If a flat, unstructured receiving element is provided, advantages may be obtained in terms of the ability of the cell carrier to be used universally. Furthermore, a defined reference surface is created which may be advantageous for optical measurements of the sample on the cell carrier. If the receiving element has a flat, structured shape, advantages may be obtained in terms of the adhesion and temporary fixing of the biological sample, in particular of a biological cell. In particular, nanostructures or microstructures with typical structure sizes in the nm to μm range may be formed, which influence the binding of the cell to the receiving element. If the receiving element has a non-planar, stepped shape, a depression may advantageously be formed which serves to determine the position of the sample and to protect it laterally. The protection of the sample on the cell carrier can be further improved if the receiving element has a cavity for receiving the sample.

According to another variant of the invention, the receiving element of the cell carrier according to the invention may be modified in terms of the choice of a specific material or the application of a coating. For example, the surface of the receiving element may be chemically modified at least in a partial region such that adhesion of biological samples, in particular of cells or cell components, is promoted or reduced. In order to promote adhesion, a fibronectin coating or a coating to form receptor/ligand combinations may be provided for example. If, on the surface of the receiving element, specific antibodies are provided to which certain cells specifically adhere, but other cells do not adhere, advantages may be obtained with regard to a cell-specific binding capacity of the receiving element.

If the receiving element of the cell carrier according to the invention has a peripheral edge, delimitation of the sample in the centre of the receiving element can advantageously be achieved. The edge may for example have an adhesion-reducing coating, on which cell adhesion is reduced or prevented. By way of example, an edge that is coated with PTFE or poly-HEMA may be provided. For practical uses, a minimum width of the coated edge of 20 µm is advantageous.

Alternatively, an adhesion-reducing coating of the edge may be omitted, and this is particularly advantageous in applications where cells on cell carriers are to be grouped to form an assembly and to this end are to grow or move over cell carrier surfaces. In this case, a minimum width of the edge can preferably be selected such that, within the desired process time (for example 0.5 to 2 h), cells move as a result of an intrinsic cell movement by means of the natural rearrangement of adhesion contacts do not move from the cell carrier to the base surface. With a typical intrinsic speed of the cells of around 100 µm/h, a lateral dimension of the surface of at least 200 µm is preferred.

If, according to the preferred embodiment of the invention, the bottom element and the receiving element are arranged one above the other and the cell carrier forms a layered structure, advantages are obtained with regard to the positional stability of the cell carrier. The layered structure is preferably dimensioned such that its thickness is smaller than 200 µm and its cross-sectional surface has a lateral dimension of less than 2 mm, particularly preferably less than 1 mm.

If, according to another variant of the invention, the cell carrier has a transparent partial region, in which the cell carrier is lucent, advantages may be obtained with regard to observation of the cell carrier, and for example with regard to ascertaining whether a sample is located on the cell carrier.

Another advantage of the cell carrier according to the invention consists in that the receiving element, the magnetic element and the bottom element can be formed in a manner adapted with great flexibility to the respective application. It may in particular be provided that the magnetic element and the bottom element form a common component. In this case, the stable support of the cell carrier is provided by the lower side of the magnetic element. Accordingly, the magnetic element can perform the function of the receiving element. In general, a cell carrier according to the invention can consist exclusively of the magnetic element, the lower surface of which forms the support on the base surface and the upper surface of which forms the receiving element for the sample, wherein in this case a particularly simple structure of the cell carrier is obtained.

Alternatively, the magnetic element on the one hand and the receiving element and/or bottom element on the other hand may form separate components. By way of example, the magnetic element may be bound in the manner of a conventional magnetic bead to the sample, which is arranged on the receiving element.

The at least one magnetic element of the cell carrier according to the invention is designed to generate a magnetic field or to interact with an externally generated magnetic field, and to this end comprises in general a magnetic or magnetizable material. According to the invention, the magnetic element may comprise a paramagnetic, ferromagnetic and/or diamagnetic material. Particular advantages with regard to effective manipulation of the cell carrier by means of an external magnetic actuator are obtained in the case of a high internal magnetization or magnetizability, so that the magnetic element preferably comprises metals, such as for example Fe or Ni, or alloys, such as for example FeSi (96% Fe, 4% Si), Permalloy or mu-metal (Ni/Fe/Cu/Cr). Furthermore, the use of paramagnetic materials such as Pt for example, or of diamagnetic materials such as Bi for example, may be provided.

Further advantages with regard to a strong magnetic interaction and flexibility in terms of the choice of material for the magnetic element may be obtained if an induction device is provided as the magnetic element. Advantageously, using microstructuring techniques, inductances can be formed for example in layer form on solid surfaces such as the underside of the receiving element which exhibit a small height and nevertheless a high magnetic interaction. As the magnetic element, a coil with at least one winding and possibly with a coil core, for example made of Fe, may be provided for example. Advantageously, there are no restrictions with regard to the coil shape. If a coil is formed in an annular manner as a cylinder coil, advantages may be obtained with regard to a high magnetic field strength. A coil which is wound in a reference plane parallel to the receiving element and the bottom element has the advantage that the height of the cell carrier can be kept small.

Another advantage of the invention consists in that there are no restrictions with regard to the shape of the magnetic element and its arrangement in the cell carrier. Rather, the configuration of the magnetic element can be selected as a function of the specific use of the cell carrier. If the magnetic element is for example a continuous layer of magnetizable or magnetic material which runs parallel to the bottom element, a high magnetic force can advantageously be achieved.

Alternatively, the magnetic element may comprise a number of partial elements which are distributed in the body of the cell carrier, wherein additional functions of the magnetic element can be achieved. If the partial elements (or an individual magnetic element) are arranged at a distance from at least one lateral edge of the cell carrier, mutual interactions between neighboring cell carrier can be reduced. To this end, the magnetic element is preferably located in the centre of the cell carrier. Alternatively, the magnetic element or a number of partial elements may be arranged even at the edge of the cell carrier, in order to achieve an interaction not only with an external magnetic actuator but also between neighboring cell carriers. By way of example, the cell carrier may be designed for movement in one specific direction of movement. If partial elements of the magnetic element are arranged at the front and/or rear edge with respect to the direction of movement, depending on the orientation of magnetic poles a chain-like linkage between neighboring cell carriers or the creation of a safety margin between neighboring cell carriers can be achieved. A magnetic orientation of the cell carrier can be defined by the partial elements. If the magnetic orientation coincides with a geometric preferred direction of the cell carrier, the manipulation of the latter under optical control can be facilitated.

According to another, particularly advantageous embodiment of the invention, the magnetic element or the partial elements of the magnetic element may form at least one data memory cell. Advantageously, this makes it possible to write identification information or other data to the cell carrier, which characterize the cell carrier or the sample located on the latter.

Another important advantage of the invention consists in the fact that there are also no restrictions with regard to the lateral outer shape of the cell carrier. For example, an outer shape can be formed with sections in different directions that are shaped so as to be complementary to one another. Advantageously, as a result, a number of cell carriers can be placed closely next to one another in order to form a culture carrier according to the invention (see below) and/or to achieve certain reactions between the samples. The outer shape of the cell carrier is in general the shape of the lateral edge of the cell carrier at a height at which the cell carrier has its maximum dimension. In the case of cone-shaped or pyramid-shaped cell carriers, the outer shape is formed for example by the contour of the bottom element. Alternatively, if the receiving element and/or the magnetic element forms a protrusion above the bottom element, the outer shape may be formed by the contour of the receiving element and/or the magnetic element.

If the outer shape can be represented by a polygon and accordingly is delimited by at least three straight portions, advantages may be obtained with regard to the cell carriers being placed next to one another without any gaps in order to form a culture carrier. Preferably, an outer shape is selected which allows a gap-free flat package of cell carriers of identical shape, which is the case for example with a regular hexagonal or triangular outer shape. Gap-free arrangements of a plurality of cell carriers advantageously permit the creation of closed substrate surfaces for the cultivation of cells.

Alternatively, for certain applications, it may be preferred that the cell carriers cannot be placed next to one another without any gaps or that a particularly large surface area of the receiving element is to be formed. In these cases, a rounded outer shape of the cell carrier is produced. By way of example, a circular or elliptical outer shape may be provided.

According to a further modification of the invention, a cell carrier may be equipped with at least one lateral supporting element which offers protection against undesirable tilting of the cell carrier. Such protection may for example be advantageous if external magnetic forces occur, such as for example flow forces in a culture medium or magnetic interference forces. A supporting element is preferably a bar or strip which protrudes from a side of the body of the cell carrier and may be designed to be rigid or flexible. According to one advantageous variant of the invention, supporting elements may perform an additional function when cell carriers are joined together to form a culture carrier according to the invention, in that supporting elements of neighboring cell carriers hook together with one another. Recesses may also be provided on the body of the cell carrier, said recesses being shaped in a manner complementary to the supporting elements in order to allow neighboring cell carriers to engage with one another.

If, according to another embodiment of the invention, the cell carrier according to the invention has at least one identification element, advantages may be obtained with regard to monitoring a plurality of cell carriers, for example in a manipulation device according to the invention (see below). As the identification element, an optical data carrier may for example be provided in the manner of a barcode or the above-mentioned magnetic data memory.

In general, the use of the invention is not restricted to certain size conditions. However, particular advantages for the intended biological and medical uses are obtained if the cell carrier is produced as a miniaturized component which is designed to receive individual cells or individual cell groups. The surface of the cell carrier which is provided for receiving samples (in particular the surface of the receiving element of the cell carrier) preferably has a free surface which is adapted for the adhesion of at most one cell. To this end, lateral dimensions (for example the diameter or edge length) of the surface are typically selected within the range from 10 µm to 1 cm, in particular from 10 µm to 5000 µm. The support formed on the underside of the cell carrier preferably also has a size within this range. For stable positioning and/or movement of the cell carrier on the base surface, the height of the cell carrier is preferably smaller than the smallest lateral dimension of the surface provided for receiving samples. The height corresponds to the vertical distance between the surface of the receiving element and the support formed by the bottom element. It is preferably selected within the range from 0.5 µm to 2000 µm, in particular from 1 µm to 1000 µm. By providing the miniaturized cell carrier, a tool is provided for cell-specific sample manipulation, which surprisingly can be operated with a high level of reliability and selectivity using macroscopic actuators.

In terms of the device, the invention is based according to a second aspect on the general technical teaching of providing a culture carrier for receiving biological cells, which comprises a plurality of cell carriers according to the invention. If the cell carriers are joined together in groups, a substrate is created for a plurality of cells, and this substrate is accordingly referred to here as a culture carrier. One significant advantage of the cell carrier according to the invention consists in creating an extremely flexible substrate which, depending on the specific application, can be designed in various forms, separated, combined in parts and processed in other ways.

According to a first variant, the cell carriers of the culture carrier are arranged next to one another and in lateral contact with one another. In this case, the cell carriers are not joined to one another. Lateral contact with one another is simply provided. Surprisingly, this loose combining of cell carriers is sufficient for cells on neighboring cell carriers to come into mechanical or material contact and/or for cultivation of the cells to occur. Alternatively, the cell carriers of the culture carrier can be secured to one another. An assembly of cell carriers has the advantage of increased stability. The cell carriers can also be arranged in an assembly such that they can be detached from one another or alternatively may be joined in a non-detachable manner.

According to one preferred embodiment of the invention, the receiving elements of the combined cell carriers form a plane culture carrier surface. This has the advantage of compatibility with conventional cultivation substrates. Alternatively, the cell carriers may form a non-planar, for example curved or stepped, culture carrier surface. In this case, advantages may be obtained with regard to creating cell cultures with certain geometries, as may be desired in so-called "tissue engineering".

In terms of the device, the invention is based according to a third aspect on the general technical teaching of providing a manipulation device for biological samples, which includes a base surface for positioning at least one cell carrier according to the invention and an actuator for exerting a magnetic force on the at least one cell carrier. By virtue of the manipulation device, disadvantages in particular of conventional fluidic microsystems using contactless particle manipulations in electric fields are overcome since cell manipulations can be carried out on cells which have adherent surface contact and nevertheless can be moved individually. The cell manipulations can be carried out with a high level of stability and reproducibility. For reliable operation, it is not necessary to maintain carrier flows or electric fields. Cell carriers comprising samples and/or biologically active substances can be positioned, moved and brought into interaction by predefinable space and time programs. Time schedules can be implemented which are adapted to the cultivation and interaction times that are of interest in practice, within the minute to hour range.

The base surface forms part of a cultivation device, such as for example a culture vessel or a fluidic microsystem. The movement of the cell carriers can be carried out by means of extremely small magnetic sources, which act as force elements from the external surroundings of the manipulation device via the base surface, as a result of which complete sterility of the cell carriers can be ensured. The force elements may be shaped such that any influence on neighboring cell carriers that may be present is minimized. By moving the external force elements, the cell carriers are moved inside a culture vessel or microsystem. To this end, use may be made for example of programmable x,y,z manipulators which by moving away from the channel surface can interrupt the forces on the cell carriers. Parallel operation or very rapid actuation of such manipulators carries out the ordered movement of a number of cell carriers simultaneously.

The base surface usually forms part of a component for holding the cell carrier, which is preferably layered or plate-shaped and is referred to as the holding plate (in particular the base plate or the cover plate). If the actuator is arranged on a rear side of the holding plate, which is opposite the base surface with the cell carriers, the base surface can advantageously form a free platform. On the platform, methods in particular for treating or processing individual cells or cell cultures can be clearly observed and optionally influenced by additional measures.

According to one preferred embodiment of the invention, the base surface contains at least in partial regions a magnetic or magnetizable material, the interaction of which with the magnetic element of the at least one cell carrier is weaker than the interaction of the actuator with the magnetic element. Passive, stable fixing of the cell carrier on the base surface can thus be achieved, even when the actuator is moved away or switched off.

If, according to another variant, the base surface has a flat surface, advantages may be obtained with regard to the ability of cell carriers to be displaced to all sides. Alternatively, the base surface may have a curved shape. This advantageously allows process control within closed containers, such as in vessels or hollow cylinders for example.

The functionality of the manipulation device can be considerably expanded if the base surface has a surface structure with protrusions and/or depressions. In this case, a topography is provided by means of which certain partial regions of the base surface can be optimized for certain process tasks. The surface structure comprises as shaped elements preferably at least one free area, one channel, one branching, one set of points switches, one annular path and/or courth. A free area is an unstructured partial region which is particularly suitable for cell cultivations using a plurality of cell carriers. A channel is a straight or curved, elongate partial region of the base surface with a longitudinal direction which serves to delimit the movement path of cell carriers between lateral channel walls. Special channel shapes are characterized by being split into at least two channels (branching, set of points) or a channel shape with a closed circumference (annular path). Short channels with a closed end form so-called enclosures and serve as parking positions for individual cell carriers or cell carrier groups.

According to another embodiment of the invention, the base surface may have at least one transparent region. Advantageously, it is thus possible to observe the cell carrier and the magnetic element and/or the relative positions of the two parts in particular during operation of the manipulation device.

A manipulation device according to the invention may be provided with two holding plates which form two base surfaces, the free surfaces of which face towards one another with a spacing therebetween and serve to receive cell carriers. Between the base surfaces, a reaction chamber is advantageously created, on the two walls of which the cell carriers according to the invention can be manipulated. The distance between the base surfaces, which are preferably of identical geometrical shape, may be selected in such a way that samples on cell carriers which lie opposite one another on the base surfaces can enter into interaction with one another.

If the base surface of the manipulation device according to the invention is covered with a fluid, such as a culture medium for example, advantages may be obtained with regard to setting cultivation conditions.

The actuator of the manipulation device includes at least one force element, by means of which magnetic interaction with the cell carrier can be generated. Depending on the magnetic element of the cell carrier, the force element contains a permanent magnet, a paramagnet, a ferromagnet, a diamagnet, an electrically excitable magnet (inductance) and/or a magnetic fluid. Advantageously, each of these types of force element can be produced in a miniaturized manner. This makes it possible to adapt the force element to the dimensions of the cell carrier and to provide a plurality of force elements within a narrow space.

In principle, the force elements could be arranged in a fixed position, wherein a displacement of cell carriers can be achieved by actuating neighboring force elements one after the other. However, preference is given to an embodiment of the invention in which the manipulation device is provided with a displacement device, by means of which the force elements can be displaced individually relative to the base surface.

If, according to a further embodiment of the invention, the manipulation device is equipped with a monitoring device, advantages may be obtained with regard to observing the cell carriers and controlling methods using the cell carriers. A microscope is preferably provided as the monitoring device.

In terms of the method, the invention is based according to another aspect of the invention on the general technical teaching of arranging a biological sample on a cell carrier in order to manipulate said sample, the cell carrier being positioned in a stable position on a base surface, and of moving the cell carrier or positioning it at a predetermined position by means of a magnetic force. The advantage of this method consists in moving adherently bound cells without affecting their bound state. As cell carriers, use is preferably made of the cell carriers according to the invention which have been described above. The manipulation preferably takes place using the manipulation device according to the invention which has been described above.

According to one preferred embodiment of the invention, samples on different cell carriers on the base surface are brought into interaction with one another or with active substances. Cell carriers are arranged next to one another, so that cells and/or cell components on the cell carriers can enter into for example mechanical or material interaction with one another or with active substances. If cells and/or cell components on neighboring cell carriers come into contact with one another, membrane contacts can advantageously be produced.

The invention has the following further advantages. For the first time, a practical possibility has been provided for moving cells in a nutrient solution in the adherent state, for example in microchannels, under sterile conditions and on individual cell carriers, without the necessary forces acting on the cells themselves in the process. Moreover, it is possible to group cell carriers together, to separate them again or permanently join them, to move cells from cell carrier to cell carrier, to monitor cell carriers containing cells, to form patterns and repeatedly group cell carriers and also to introduce and remove the cell carriers and cell carrier groups containing cells into and out of a manipulation device such as, for example, a microchannel system. One significant advantage of the invention is the defined and pre-determinable orientation and localization of the cells in the manipulation device and relative to one another. Random factors can largely be ruled out. By virtue of the freedom in terms of configuration when creating a culture carrier according to the invention, the geometry and material of a settlement surface for cell adhesion can largely be selected at will.

Furthermore, it is possible to observe and also image the adherent cells, for example adherently growing cells. Any known microscopy method may be used, and the imaging can be carried out with an extremely high microscope resolution.

The manipulation of the cell carriers makes it possible for the first time to obtain a free movement counter to a flow or even in different directions, for example in a channel of a manipulation device which is flowed through by a fluid. Cells can also be moved out of the manipulation device against a surface tension of an outlet opening.

Another advantage consists in that parallel manipulation of a plurality of cell carriers and movement of the cell carriers on as many wall surfaces as possible of a manipulation device is possible, so that also different cell carriers containing cells can be moved past one another or even in opposite directions. The precision of the movement may in this case lie in the micrometer and nanometer range and allow very fast (mm/s) to very slow (µm/h) movements.

BRIEF DESCRIPTION OF THE DRAWINGS

Advantageous embodiments and applications of the invention will be described below with reference to the appended drawings, in which:

FIGS. 2 and 3 show perspective views of further embodiments of cell carriers according to the invention, FIG. 4 shows top views of different embodiments of culture carriers according to the invention.

DETAILED DESCRIPTION OF THE INVENTION

The invention will be described below with reference, by way of example, to schematically illustrated basic shapes of cell carriers and culture carriers. It is pointed out that the implementation of the invention is not limited to the examples illustrated, but rather can be embodied in particular with modified shapes, sizes and materials which are adapted to the specific purpose of an application.

Figure 1:
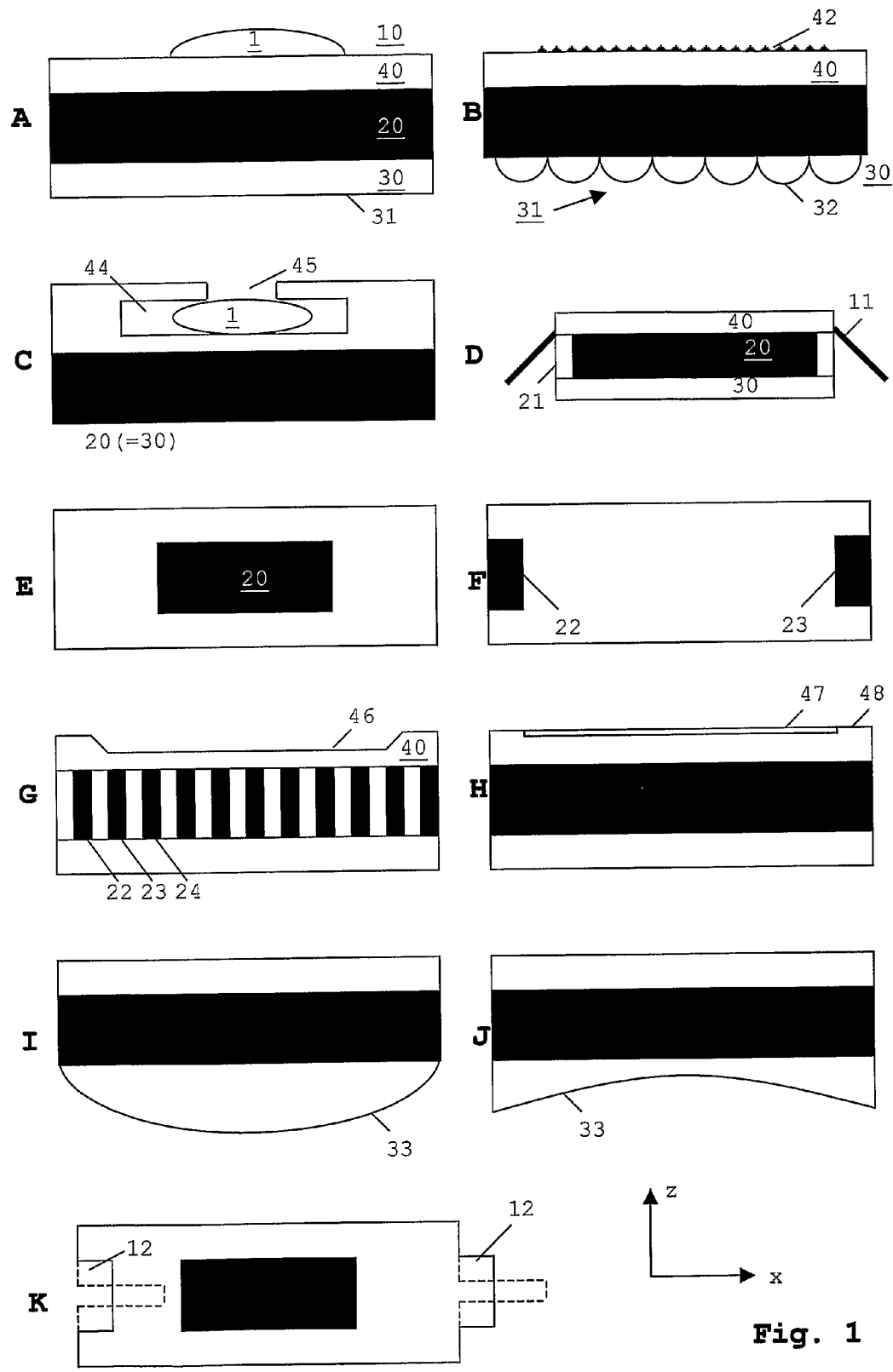
FIG. 1 shows sectional views of different embodiments of cell carriers according to the invention.

FIG. 1 shows, in the partial images A to M, vertical sectional views of cell carriers 10 according to the invention, which in each case comprise the magnetic element 20, the bottom element 30 and the receiving element 40. These elements may comprise different parts or be formed by common parts. According to the invention, the cell carrier 10 usually has the shape of a plate or disc, the thickness (or height) of which is smaller than the minimum lateral dimension. The plate shape extends essentially in an x,y plane which runs parallel to the orientation of a flat base surface of a manipulation device (see below). In most examples, the elements 20, 30 and 40 are arranged one above the other, essentially as a stack. The cell carriers are produced by means of micromechanical or microchemical methods of microstructure technology, which are known per se, for example from silicon, glass and/or plastic.

As shown in FIG. 1A, the magnetic element 20, the bottom element 30 and the receiving element 40 in each case have a layer form. The magnetic element 20 contains iron and has a thickness in the range from 100 nm to 500 µm, preferably in the range from 1 µm to 100 µm, for example 40 µm. The bottom element 30 consists of a layer which forms a continuous flat support 31, for example made from PTFE. The support 31 advantageously forms a protective layer between the magnetic element 20 and the surroundings. The PTFE layer has a thickness of a few µm. The receiving element 40 is a plastic layer, for example made from polyethylene (PE) or polyurethane (PU), with a thickness of 0.1 µm to 100 µm. A cell 1 is arranged on the receiving element 40. According to FIG. 1A, the elements 20, 30 and 40 have the same outer shape in the x,y plane, so that they form a straight stack. The cross-sectional surface perpendicular to the z direction is for example circular with a diameter of 300 µm. The lateral dimension of the cell carrier is for example within the range from 10 µm to 1 cm and is preferably less than 2 mm, particularly preferably less than 1 mm, while its height has a value for example in the range from 1 µm to 1000 µm and is preferably less than 200 µm.

The bottom element 30 and the receiving element 40 may have surfaces which are both made from the same material (for example PE or PU), so that the structure of the cell carrier in the z direction is symmetrical with respect to a central plane. This symmetry may be advantageous with regard to the handling of the cell carrier.

The loading of the receiving element 40 with the cell 1 or with cell components may be effected by means of dispensing techniques which are known per se, for example by means of a pipette. Alternatively, a movement over neighboring cell carriers may be provided by means of an intrinsic movement of the cell. If the receiving element 40 is provided with only a cell track as the cell component, as left behind as a material residue by migrating cells on substrates, the loading may take place by the cell moving over the receiving element 40.

FIG. 1B illustrates the cell carrier with a bottom element 30 which comprises a plurality of hemispherical or semicylindrical structures with support points 32 which lie in a common plane and which form the support 31, and exhibits reduced friction on a base surface compared to FIG. 1A. Furthermore, FIG. 1B shows that the receiving element 40 has in the centre, as a structured surface 42, a roughened area with typical structure dimensions of, for example, 0.01 µm to 100 µm.

In FIG. 1C, the receiving element is formed with a cavity 44 which has an opening 45. Through the opening 45, a cell 1 can be deposited in the cavity 44. FIG. 1C furthermore illustrates that the function of the bottom element 30 is performed by the magnetic element 20.

The supporting elements 11 illustrated in FIG. 1D serve in particular to protect against tilting of the cell carrier. The supporting elements 11 are formed as laterally protruding strips which point towards the floor, said strips being formed for example in one piece with the material of the receiving element 40 or of the bottom element 30. The magnetic element 20 in this example has a layer form, which does not run through the entire body of the cell carrier, but rather is separated from the surroundings at the edge by a protective layer 21, for example made of plastic. The protective layer 21 may also be formed in one piece with the receiving element 40.

According to the invention, it may be provided that the supporting elements 11 partially or fully perform the function of the bottom element 30. For example, the bottom element 30 shown in FIG. 1B may have just one or two support points 32 which, together with at least one further supporting element 11, form the desired stable support. Moreover, the cell carrier may rest entirely on at least three supporting elements 11.

If the protective layer 21 is selected to be particularly thick, the central arrangement of the magnetic element 20 in the body of the cell carrier is obtained as shown in FIG. 1E. The magnetizable or magnetic region is restricted to a central part of the body, so that magnetic interactions between the neighboring cell carriers can thus be kept small or can be prevented (see also FIG. 12).

In FIGS. 1F and 1G, the magnetic element 20 comprises a number of partial elements 22, 23, 24 distributed in the cell carrier 10. The partial elements 22, 23 at edges of the cell carrier (FIG. 1F) may influence the interaction with neighboring cell carriers (chain formation or repulsion, depending on the distribution and pole arrangement of the partial elements). FIG. 1F also shows that the receiving and bottom elements can be produced in one piece from one material, for example in the form of a circular disc or a flat square, in which the partial elements 22, 23 are inserted at the sides. Alternatively, the partial elements 22, 23 may be applied in layer form to the cell carrier body (see FIGS. 2A, C).

The partial elements 22, 23, 24 at edges and in the interior of the cell carrier (FIG. 1G) can be used as data memories. They comprise for example separately magnetizable particles or domains of a magnetic element, the directions of magnetization of which can be set individually by means of a magnetic field.

FIG. 1G illustrates a structuring of the receiving element 40 by means of a stepped formation, so that a depression 46 is formed. For example, the depression 46 is milled or etched by means of microstructuring techniques which are known per se, into the receiving element 40 to a depth of for example 0.01 μm to 100 μm, so that effective lateral protection is formed for adhering cells. An adhesion-promoting coating 47 may be provided on the bottom of the depression 46 or in general on the surface of the receiving element 40 (FIG. 1H), said coating covering at least a partial region, for example the centre of the surface 41. The coating 47 consists of fibronectin with a thickness of 10 nm to a few μm. It is surrounded by an adhesion-reducing edge 48 made from PTFE. Alternatively, the coating may contain physiologically active molecules for generating interactions with the cells.

Figure 15:
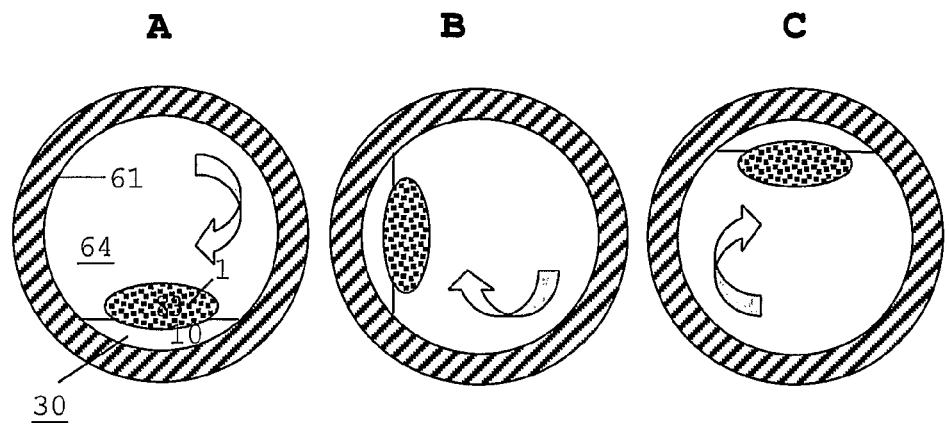
FIGS. 15 and 16 show illustrations of embodiments of manipulation devices according to the invention with curved base surfaces.
Figure 16:
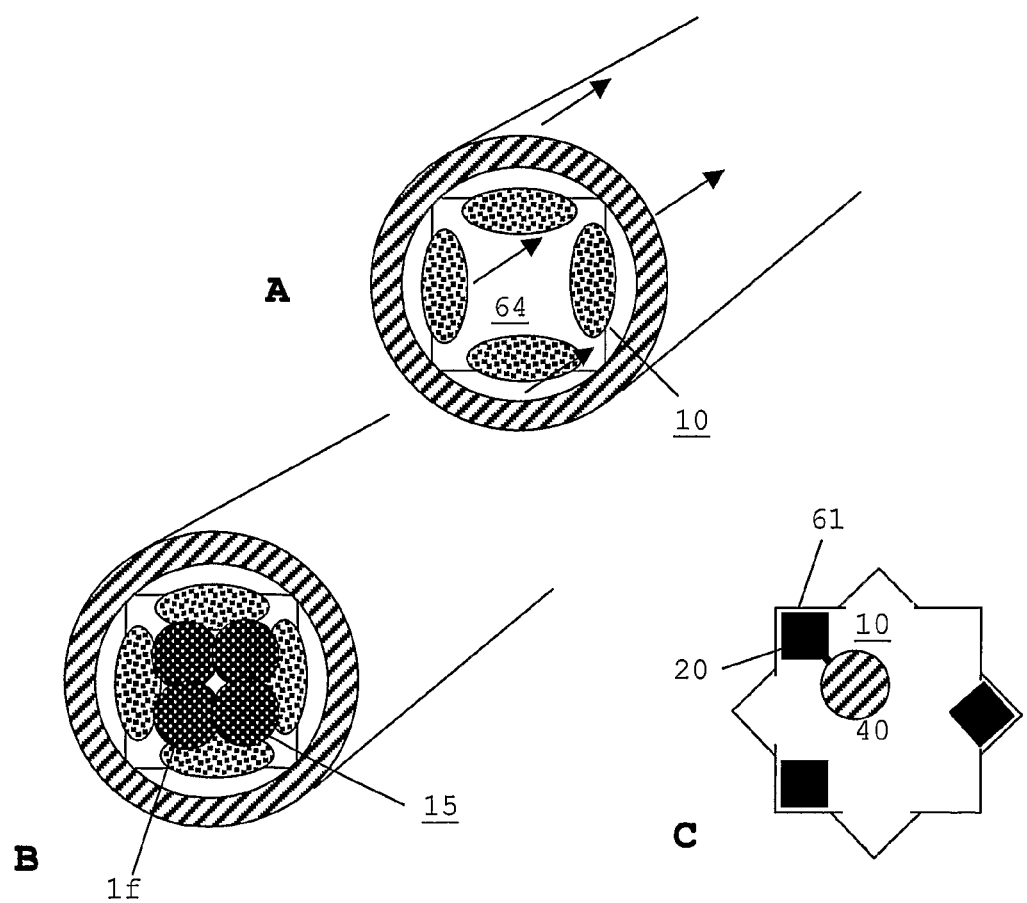

FIGS. 1I and 1J illustrate cell carriers with bottom elements which form a profiled support 33 with a convexly or concavely curved support profile. With their cylindrical support profiles, these cell carriers are suitable for stable support on curved base surfaces, which are shown in FIGS. 15 and 16.

FIG. 1K shows lateral securing elements 12 which are located on the sides of the cell carrier as protrusions and recesses with shapes that are complementary to one another. They serve to secure neighboring cell carriers to one another, and optionally serve as supporting elements if they have a sufficient lateral dimension (see variant shown in dashed line). Secure cell carrier connections, which optionally can no longer be released, may be advantageous for example at the outputs of a microchannel system, if a cell carrier group is to be transferred to a new system or a cultivation chamber. In this way, a high degree of automation can be achieved, as desired for applications in biotechnology.

In FIG. 1L, the magnetic element 20 and the bottom element 30 are provided as separate parts. By way of example, the magnetic element 20 may be bound in the manner of a conventional magnetic bead to the sample 1, which is arranged on the surface of the bottom element 30.

FIG. 1M illustrates a variant of the cell carrier with a spherical receiving element 40, which is characterized by an increased adsorption surface.

FIG. 2 shows further embodiments of the cell carrier 10 in schematic perspective view. Like FIGS. 1B and 1H, FIGS. 2A and 2B illustrate surface regions 40 (structured fields) to which cells 1 can adhere well and survive. In FIG. 2A, the identification element 13 is applied to the surface of the support element in the form of a barcode.

The surface regions 42 to which cells 1 adhere well may extend as strip-shaped run paths 42A to the edge of the cell carrier (see FIG. 2B). In the joined state as a culture carrier (see FIG. 4), the run paths 42A can cooperate for cell migration between neighboring cell carriers.

The magnetic elements 20 of the cell carrier 10 are designed in a compact manner (FIG. 2A), as an inserted layer (FIG. 2B), as inserted partial elements (FIG. 2C) or as a lower coating (FIG. 2D). The important thing is that the cell carrier 10, by the internal magnetic field or in an external magnetic field, does not tend to rotate or tilt. Therefore, cells cannot be pushed onto channel walls or a base surface (see below) and adhere there.

The geometry of the cell carrier 10 can be freely selected within wide ranges, for example in order to make it easier to join them together or determine the orientation thereof. FIGS. 2A to 2C show a polygonal outer shape 14 with a preferred direction (A, B) or with a hexagonal symmetry (C).

According to other variants (not shown), the cell carrier has a regular octagonal, rectangular, square, elliptical or circular basic shape.

FIG. 3A shows the cell carrier 10 in the form of a truncated cone or pyramid with the depression 46 in the central region, in which one or more cells 1 can settle, said cells receiving a certain amount of protection as a result of this geometric shape. The magnetic element 20 in layer form is covered by the bottom element 30 with respect to the floor side. The illustrated embodiment has excellent positional stability while at the same time exhibiting freedom in terms of the configuration of the surroundings of the cell cultivation surface. In FIG. 3, the receiving element of the cell carrier 10 is produced for example by anisotropic etching from silicon.

FIG. 3B shows the cell carrier 10 with a magnetic element which comprises partial elements 22, 23. The cell carrier 10 consists of a transparent plate, for example made of glass or plastic, on the surface of which a structured, light-impermeable coating 42 is provided as the receiving element 40. A circular cutout 43 is formed in the coating 42. The cutout 43 forms a transparent observation area which allows optical observation of a sample on the receiving element 40. The transparent cell carrier is exposed at the edge of the coating 42. In a manner analogous to the variant shown in FIG. 2B, run paths 42A are provided for cell movement to neighboring cell carriers.

Embodiments of culture carriers 50 according to the invention, which in each case comprise a plurality of cell carriers 10, are shown in FIG. 4. Variants A to D illustrate how ordered, patterned arrangements can be formed from cell carriers 10 with identical or different geometric outer shapes.

Since the cell carriers form patterns with a continuous surface, the culture carriers 50 have closed culture carrier surfaces 51 which are used as substrates for cell cultures or cell monolayers with a high level of adaptability for the specific application. Advantageously, due to the flexibility in joining the cell carriers together, cell cultures can be created with a defined positional arrangement of specific, optionally different, cells.

The variant shown in FIG. 4A with regular hexagonal cell carriers has the advantage that the cell carriers can be joined together with a large surface of the individual cell carriers to form a single surface. The variant shown in FIG. 4D with arrow-shaped cell carriers has the advantage that a geometric preferred direction is provided which can be detected from outside or optically. The arrow-shaped cell carriers have the shape of a strip with a point tip at one end (the front end) and an indentation at the opposite end (the rear end). The point and the indentation are shaped so as to be complementary to one another. The front and rear ends define the geometric preferred direction, which preferably coincides with a magnetic orientation of the magnetic element or the parts thereof. Other cell carriers may have points or indentations at both ends.

Figure 5:
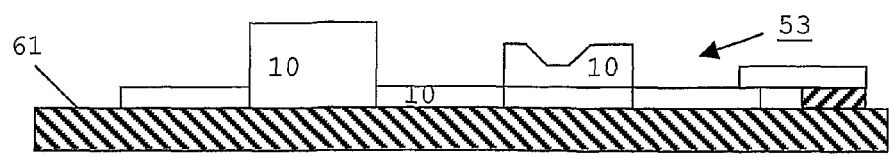
FIG. 5 shows a sectional view of a further embodiment of a culture carrier according to the invention.
Figure 6:
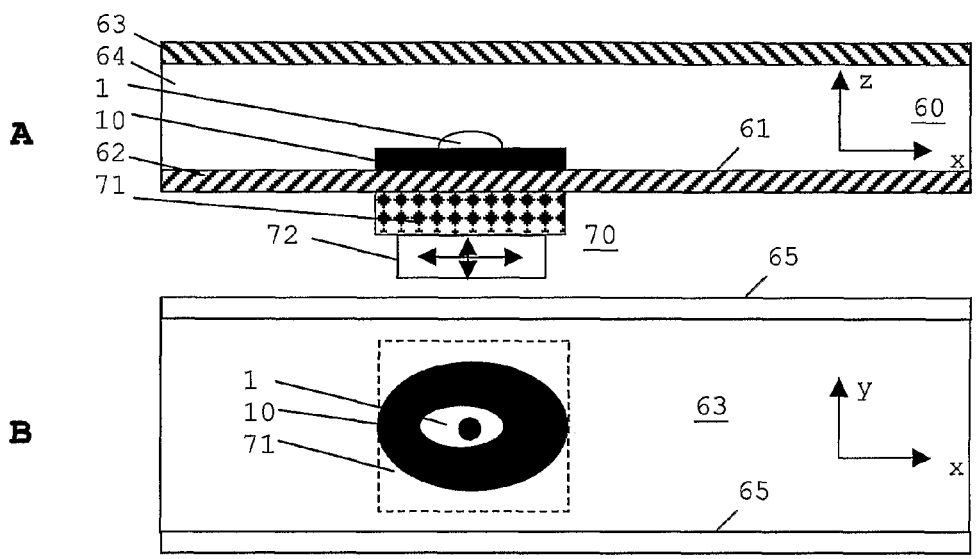
FIG. 6 shows illustrations of one embodiment of a manipulation device according to the invention.

Another degree of freedom in terms of the configuration of cell cultures on culture carriers 50 according to the invention is shown in FIG. 5. If cell carriers 10 of different height are combined on a common base surface 61, a culture carrier surface 53 with a stepped topography is obtained. In this case, the cell carriers may be arranged next to one another, sliding one above the other or hooked or secured to one another.

Details regarding manipulation devices 60 according to the invention for biological samples are illustrated in FIGS. 6 to 16. In general, the manipulation device 60 comprises a solid base surface 61, on which at least one cell carrier 10 can be positioned and moved, and an actuator 70 for exerting a magnetic force on the cell carrier 10. This combination can be achieved according to the invention by means of various devices for cell cultivation, such as, for example, by means of culture dishes or other working platforms. The following description relates to the preferred embodiment of the manipulation device 60 with a fluidic microsystem, which is characterized by a miniaturized structure of fluid-filled compartments and channels for receiving the cells that are to be manipulated. Fluidic microsystems and the production thereof from structured base and cover plates, which are separated from one another by spacers, for example made of plastic, glass and/or semiconductor materials, are known per se and therefore the details thereof will not be described here.

Hereinbelow, reference will be made to horizontally oriented Microsystems. The invention can be implemented in a corresponding manner with vertical base surfaces or with base surfaces inclined in some other way, so long as it is ensured, due to inherent magnetic binding by means of the actuator or another adhesion mechanism, that cell carriers in the resting state are not displaced under the effect of gravity.

FIG. 6A shows, as part of the manipulation device 60 and in sectional view, a channel 64 which is formed between a base plate 62 and a cover plate 63. The solid base surface 61 is formed by the surface of the base plate 62 which faces towards the channel 64. The base and cover plates 62, 63 are transparent and are made for example from glass, silicon and/or plastic material with a thickness of, for example, 50 μm to 3 mm. The distance in the z direction between the base and cover plates 62, 63 is for example 10 μm to 5 mm. The channel width in the y direction is for example 40 μm to 10 mm. The channel 64 is filled with a fluid which may flow or be at rest. If the fluid is a physiological medium or nutrient medium, cells on the cell carrier 10 are able to survive and may possibly even grow and multiply on the cell carrier. The surfaces of the base and cover plates may be coated at least in partial regions with PTFE or a similar adhesion-reducing material. A channel has for example the following dimensions: height less than 1 mm, width less than 10 mm, preferably less than 5 mm, length: depending on the specific application, for example cm to m range.

According to the invention, the cell carrier 10 with at least one cell 1 is held in a magnetic field from outside by the actuator 70, through the channel wall (here: base plate 62). The growth side of the cell carrier 10 is always directed towards the channel 64. The actuator 70 comprises at least one force element 71, which in this case is a permanent magnet, a magnetizable particle or a coil. The force element 71 can be moved mechanically relative to the base plate 62 by means of the displacement device 72. Depending on the specific application, the movement takes place in at least one direction of advance, for example parallel to the longitudinal direction of the channel (x direction), and in general in all spatial directions. The displacement device 72 comprises a servo motor or a piezoelectric drive. Due to the flat design and small size (for example for moving adhering human cells or mammalian cells having a diameter of 10 μm to 100 μm), the cell carrier can be held in a defined position and can be moved on the inner side of the channel 64 with an accuracy of <0.1 μm without adversely affecting the sterility.

FIG. 6B shows the arrangement of the cell carrier 10 with the cell 1 on the base plate 62 between channel side walls 65, in top view. The cell carrier 10 has an elliptical outer shape, which differs from the shape of the force element 71 shown in dashed line. In each operating state, the cell 1 is at a sufficient distance from the walls of the channel 64.

Figure 7:
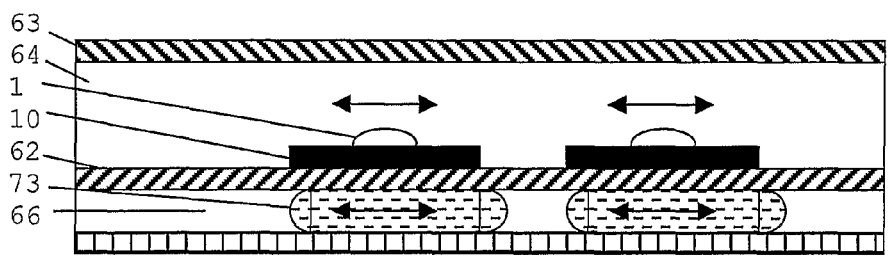
FIGS. 7 and 8 show side views of further embodiments of manipulation devices according to the invention.

As shown in FIG. 7, the force element may be formed by droplets 73 of a magnetic fluid which are moved in a further channel 66, said further channel being fluidically separated from the first channel 64. The movement of the magnetic fluid takes place as a continuous or interrupted fluid flow in the channel 66. The magnetic fluid is an oil in which magnetic or magnetizable particles are dispersely distributed. The magnetic droplets 73 are separated from one another by fluid regions with which the magnetic fluid is immiscible. In this way, cell carriers can move one behind the other at predefinable, constant distances. In an analogous manner, use may be made of force elements for example in the form of permanent magnets or coils.

Figure 8:
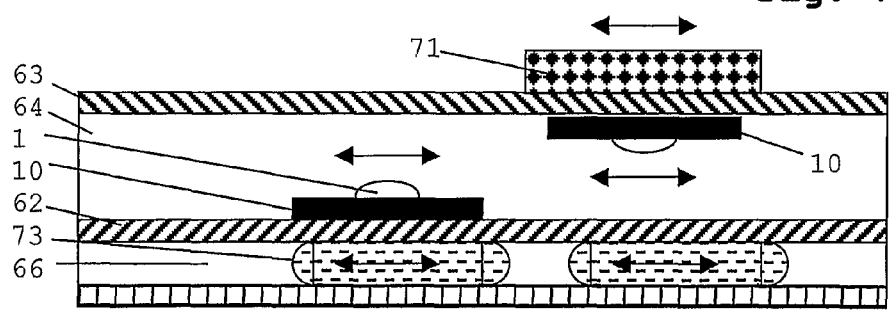

The movement of a plurality of cell carriers 10 may take place on different channel walls, as shown in FIG. 8. A first cell carrier 10 is moved by the force element 73 of a first actuator on the base plate 62 while, independently thereof, a second cell carrier 10 is moved by the force element 71 of a second actuator on the cover plate 63. The actuators may be of identical types or, as shown, of different types.

Figure 9:
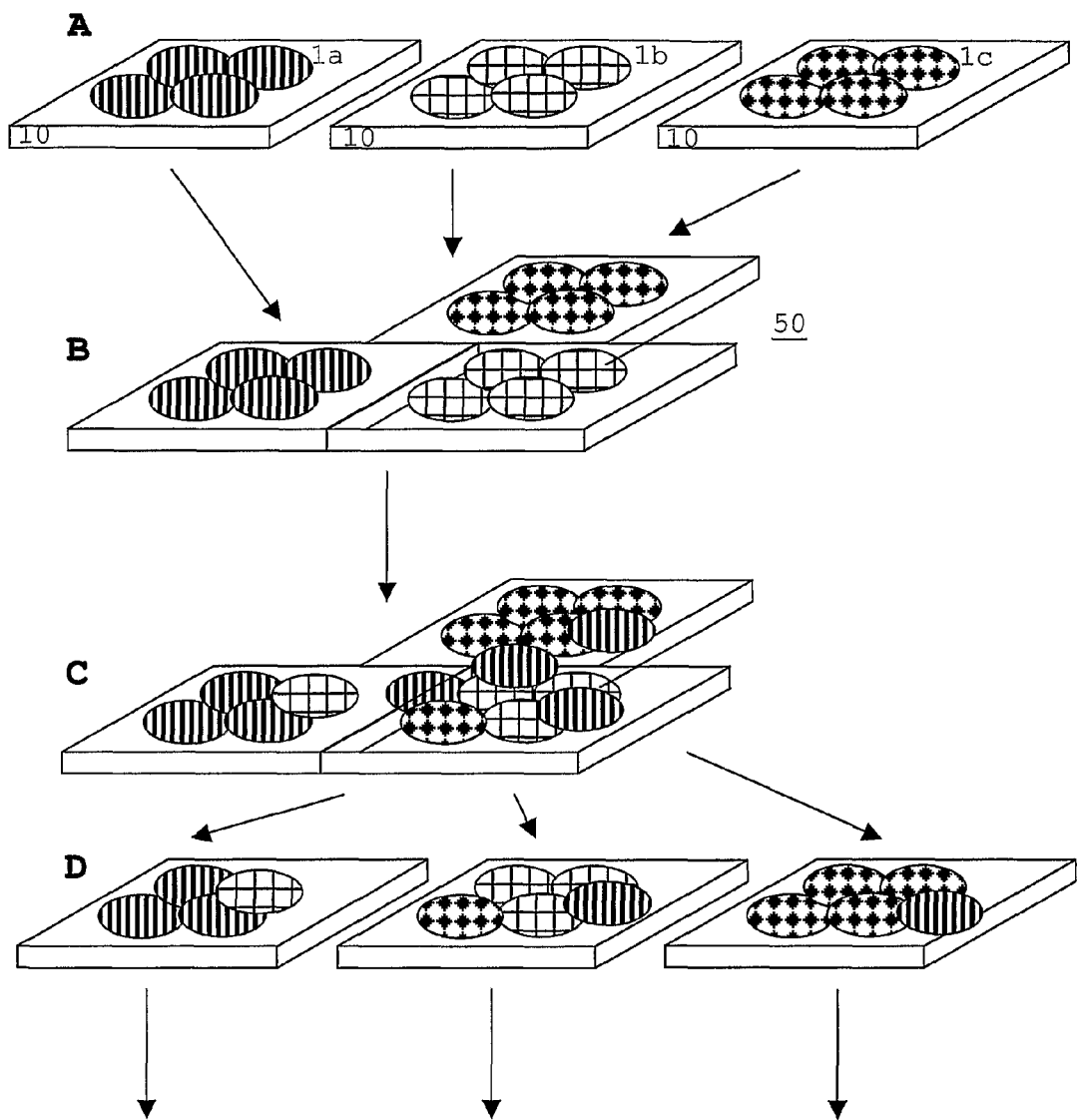
FIGS. 9 and 10 show illustrations of embodiments of the cell manipulation methods according to the invention.
Figure 10:
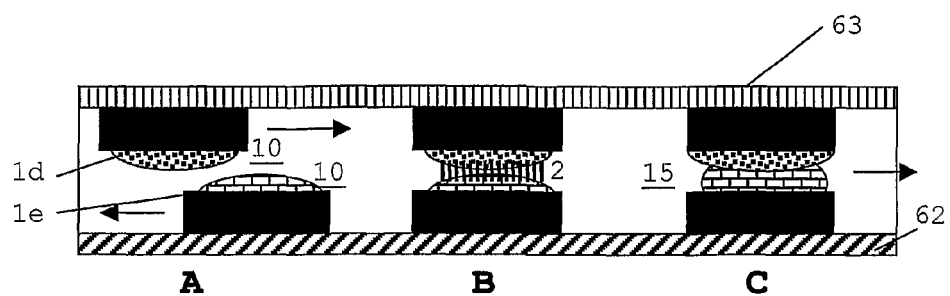

FIGS. 9 and 10 illustrate embodiments of methods according to the invention, in which cell carriers 10 are usually positioned next to one another so that cells and/or cell components on the cell carriers can enter into interaction with one another. In this case, for example, a cell movement from one cell carrier to a neighboring cell carrier (FIG. 9) and/or an adhering interaction between cells on different cell carriers (FIG. 10) is provided.

In order to handle different cell types 1a, 1b and 1c, these are firstly provided on separate cell carriers 10 (FIG. 9, step A). The loading of a cell carrier with a cell takes place for example by a sedimentation process in a culture medium, using an optical tweezer or by means of dielectrophoretic manipulation. In the manner described above, the cell carriers 10 can be joined together, for example in a channel system or another fluid volume, to form a culture carrier 50 (FIG. 9, step B). By virtue of their intrinsic active movement or via filopodia, the cells can then seek contact with one another and form aggregates, which are desirable (FIG. 9, step C). Thereafter, the resulting groups can if necessary also be separated again (FIG. 9, step D), for example in order to be subjected to further cultivation.

According to the procedure shown in FIG. 9, it is possible for example for adult stem cells of animal or human origin, blood cells, cancer cells or immune cells to be brought into interaction with one another.

The process illustrated in FIG. 9 has the advantage that the cells can be brought into interaction with one another in the adhering state in a predetermined manner, gently and without any non-physiological stress on the cells.

FIG. 10 shows, in three steps A, B and C, essential phases of contact and bonding between different cells 1d, 1e on different cell carriers 10. The cell/cell contact plays an important role in tissue engineering and in particular also for stem cell therapies in the medical sector when "imprinting" cells with the aim of, for example, differentiating within a specific cell type. In a manner analogous to FIG. 8, cell carriers 10 on which the cells 1d, 1e that are to be brought into contact with one another are located can be moved independently on the base and cover plates 62, 63 of a channel or of a compartment (step A). By means of magnetic forces, the cells are placed one above the other so that a gap of less than 10 μm remains between them (step B).

Most animal and human cells then start to automatically extend their filopodia 2 and actively seek contact with one another (shown in step B by black lines between the cells). Local contact is then actively established, until intensive and extensive cell contact is achieved (step C). As the method continues, the cell carrier assembly 15 consisting of two cell carriers which point towards one another with their receiving elements and which are connected via the adhering cells can then be subjected to a further movement and/or manipulation, in particular in a manner corresponding to the technique according to the invention.

Figure 11:
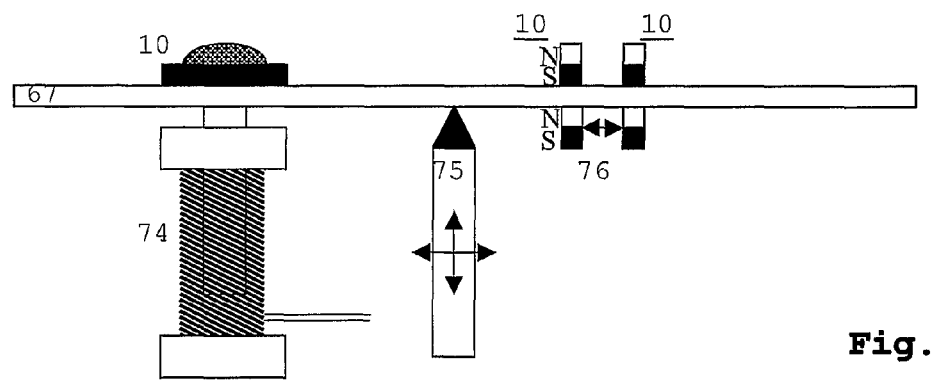
FIGS. 11 and 12 show illustrations of the exertion of force on cell carriers according to the invention.
Figure 12:
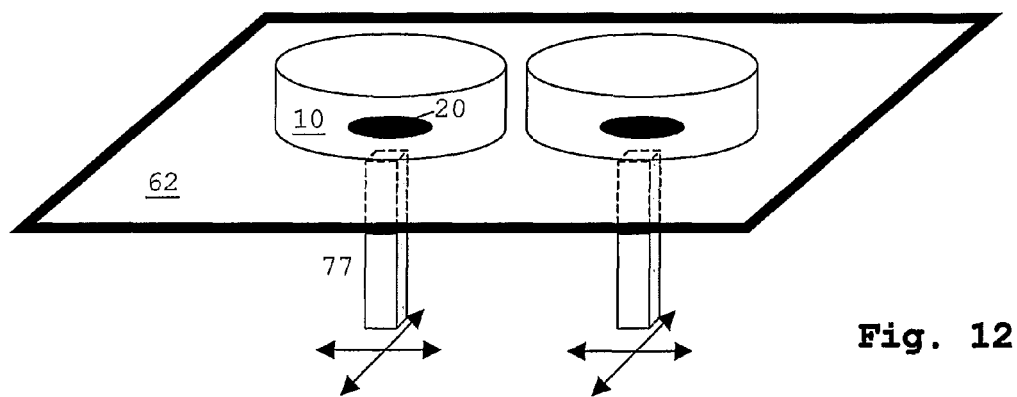

FIGS. 11 and 12 illustrate further details regarding the force elements of magnetic actuators. Below the holding plate 67 on which a cell carrier 10 with a cell is located, magnets 74, 75 and 76 of various shape are illustrated in FIG. 11, which magnets are guided along the holding plate 67 and then displaced laterally in order to move cell carriers from outside. In order to form magnetic fields which are as local as possible, small armatures (74), tips (75) and/or permanent magnets (76) may be used. The side of the magnet which faces towards the holding plate 67 may be much smaller than the cell carrier 10. By virtue of a suitable choice of permanent magnet, repelling forces can also be built up if cell carriers come too close to one another (76).

According to one modified variant (not shown), a force element comprises a cylindrical structure with a permanent-magnetic core (diameter approximately 2 mm) and an outer housing (diameter approximately 8 mm) for protecting the core, for holding the force element in the actuator and optionally for field generation. The permanent-magnetic core is embedded for example in plastic, e.g. in PVC, in the housing, which is made for example of iron or steel. Instead of the permanent-magnetic core, an electrically excitable coil may be provided.

FIG. 12 schematically illustrates a device structure for a complex multichannel system. A plurality of cell carriers 10 according to FIG. 1E (cells not shown), which can be moved independently of one another, are located on the base plate 62 of a microsystem. With rod-shaped force elements 77, the cell carriers 10 can be guided around one another in the plane of the base plate 62 and to any desired position. The rod-shaped force elements 77 consist for example of a carrier rod, at the free end of which a permanent magnet or a magnetizable particle is located. In order to move the rod-shaped force elements 77, use is made of x,y,z displacement units with an accuracy in the μm range which are known per se. Depending on requirements, a plurality of force elements 77 which can be actuated in parallel may be arranged below the base plate 62. Even if the dimensions of the channels are in the micrometer to millimeter range, entire systems of considerable surface dimensions can be produced. This may even go as far as plates in the square meter range which are made of glass, plastic, ceramic; silicon, etc.

The base surface 61 of a manipulation device 60 according to the invention preferably has a surface structure 80 with protrusions and/or depressions, by means of which different regions with specific functions can be delimited from one another. In the case of fluidic Microsystems, the surface structure 80 is formed by the separating walls, for example of channels or compartments. The variability in terms of the configuration of microsystems, the surface structure of which comprises free areas 81, channels 82, branchings 83, annular paths 84 and enclosures 85, is shown by way of example in FIGS. 13 and 14.

Figure 13:
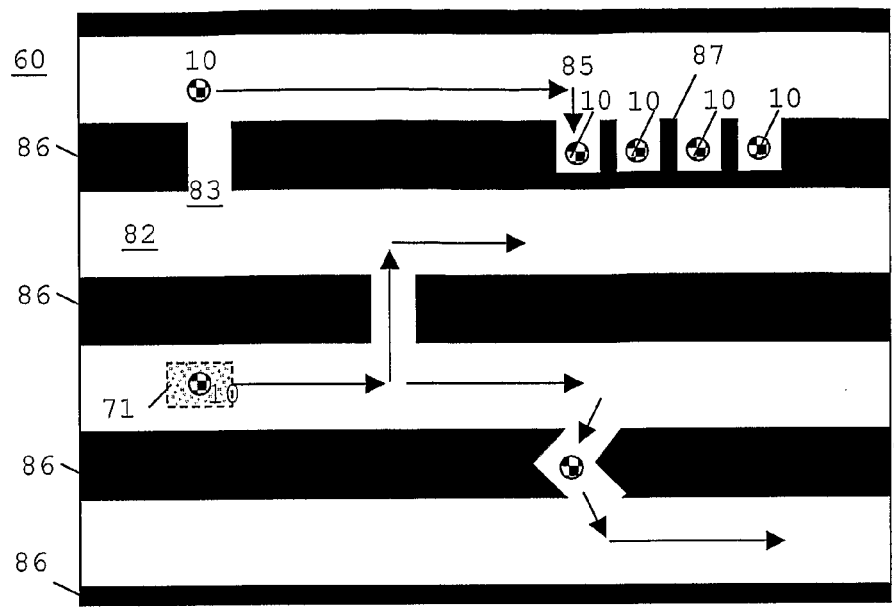
FIGS. 13 and 14 show top views of further embodiments of manipulation devices according to the invention.

FIG. 13 illustrates a four-channel system in top view, wherein light regions indicate fluid-filled channels 82 whereas black regions indicate channel walls 86 and spacer regions 87. In the light regions, the base surface for the cell carriers is transparent. Round cell carriers 10 (shown here without cells) can be moved in the direction of the arrows on the base plate 62 by means of a magnetic or magnetizable force element 71.

Important basic elements which are used with preference in Microsystems for combining and cell growth purposes (from the individual cell to the cell group) comprise branchings 83 with passages between the channels 82 and courts 85 which can be used as parking positions for cell carriers (FIG. 13). Channels which run in parallel can also be used as overtaking paths. Combining such elements makes it possible to design complex microchannel systems for cell manipulation and in vitro cultivation under absolute sterility, with many possibilities for example with regard to observation and illumination.

The courts 85 form protected rest positions for the cell carriers, at which certain method steps can be carried out, such as, for example, culture growth, interaction with an active substance and/or the formation or fixing of the bond of the cell to the cell carrier.

Manipulation devices according to the invention (in particular microchannel systems) may furthermore be equipped with optical, electrical and fluidic components. For example, electrodes for generating electric fields (electroporation, electrofusion, electroosmosis, dielectrophoresis, electrophoresis) may be provided.

Figure 14:
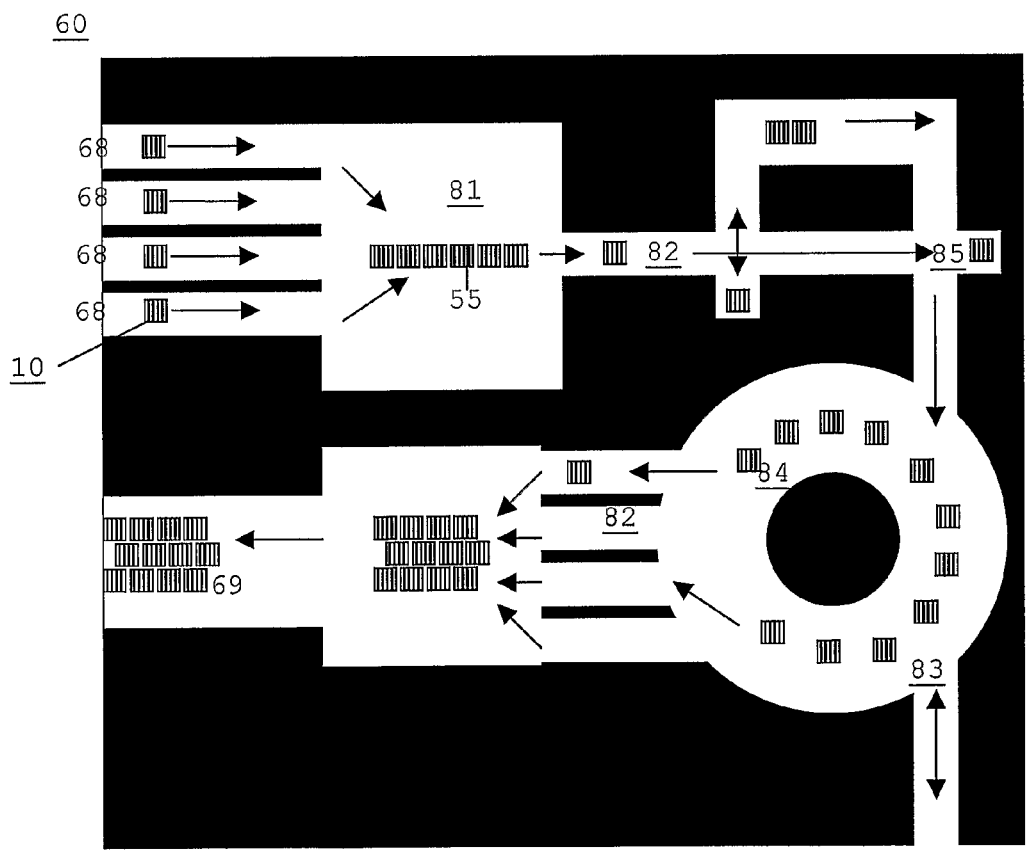

FIG. 14 illustrates a method in which firstly cell carriers 10 with certain cells are placed at parallel inputs 68 of the manipulation device 60. The free area 81 forms a grouping region for forming a cell carrier chain 55, the individual cell carriers of which are transferred to the channel 82 for carrying out specific interactions in enclosures 85, an intersecting channel or a neighboring channel, which forms a parking loop. Furthermore, the cell carriers may be arranged on an annular path 84 which forms a cell carrier combining or grouping ring. From the annular path 84, a branching 83 may lead to a further channel 82 or forwards to outputs 69.

FIG. 14 illustrates the universal possibilities of cell carrier manipulation and grouping, as required for tissue engineering and the "imprinting" of cells above the surfaces thereof in biotechnology. It is also possible for much more complex channel systems to be developed and networked and combined with one another in an analogous manner.

The implementation of the invention is not restricted to rectangular structures. FIG. 15 shows a cell carrier 10 according to FIG. 11 on a curved base surface 61, which is formed by the inner wall of a hollow cylinder, for example of a capillary. The internal volume of the hollow cylinder forms a channel 64 which is flowed through by fluid. Given a suitable formation of the bottom element 30 of the cell carrier 10, the latter with cells 1 can be moved in a desired manner to all sides (partial images B and C). This results in a very large number of possibilities for providing a certain proximity between cells. In particular, a solution is provided to the problem of the defined grouping of different or identical cell types, which is used in particular in tissue engineering.

FIG. 16 shows by way of example further basic configurations for cell aggregation. Located in a cylindrical channel 64 are four cell carriers 10, on which identical or different cells 1 are located. The latter can make contact with one another at the sides (16A) or else can fill the remaining internal space by multiplying, so that even there cells if can be found (16B). As a result, a coherent cell carrier assembly 15 is created from the four cell carriers, and this assembly can in turn be further manipulated: as one unit. The cells in the inner part may also be cells that have been flushed in via the fluid or may be synthetic bodies, so that widely ranging and variable shapes of the defined formation of aggregates are available for biotechnology.

At this point, it should be mentioned that the magnetic forces can be made to be high enough also to separate a cell aggregate again. This cannot be achieved with most other methods (dielectrophoresis, optical tweezers, etc.), but is a basic requirement of tissue engineering. This process can be carried out quickly, whereby cell damage has to be taken into account, or else can be carried out at a speed which corresponds to the rate of fluctuation of the adhesion contact of the cells. These would then be movement speeds in the range from a few to several hundred μm/h. Such speeds can easily be achieved via the external magnetic fields.

FIG. 16C shows an angular channel in cross section, which forms an angular base surface 61. Cell carriers 10 with magnetizable or magnetic magnet elements 20 (black) can be moved in paths, grooves, etc. Arranged on these as receiving elements 40 are for example spherically shaped parts to which the cells (not shown here) can again adhere. In this way, a certain distance of the cells from the channel surface is achieved, and this helps to prevent any adhesion of the cells to the channel wall. Rails, guides and thickened/thinned sections in the channel shape can be formed in an analogous manner.

The features of the invention which are disclosed in the above description, the claims and the drawings may be of significance both individually and in combination with one another for implementing the invention in its various embodiments.

The invention claimed is:

1. A method for manipulating biological cells, comprising the steps of:
    positioning at least one biological cell on at least one cell carrier, wherein the cell carrier comprises a bottom element, which is arranged such that it can be placed and shifted on a solid surface wherein the bottom element of the cell carrier and the solid surface are in physical contact, and wherein the cell carrier has a lateral dimension within the range from 10 μm to 1 cm and a height within the range from 0.5 μm to 2000 μm, and
    moving the cell carrier with the at least one biological cell on the base surface by exerting a magnetic force.

2. The method according to claim 1, in which a number of cell carriers are positioned next to one another, so that cells and/or cell components on the cell carriers enter into interaction with one another.

3. The method according to claim 2, in which cells, capable of migrating, move between neighboring cell carriers.

4. The method according to claim 2, in which cells and/or cell components on neighboring cell carriers make contact with one another.

5. The method according to claim 4, in which cytological imprinting of cells on neighboring cell carriers takes place.

6. The method according to claim 4, in which a magnetic force acts on the cells and/or on the cell carrier.

* * * * *